United States Patent
Eddo et al.

(10) Patent No.: US 10,195,316 B2
(45) Date of Patent: Feb. 5, 2019

(54) SYSTEM AND METHOD FOR PROVIDING PRESSURIZED INFUSION AND INCREASING OPERATING ROOM EFFICIENCY

(71) Applicant: ABBOTT MEDICAL OPTICS INC., Santa Ana, CA (US)

(72) Inventors: Collin Eddo, Santa Ana, CA (US); Timothy L. Hunter, Corona Del Mar, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 263 days.

(21) Appl. No.: 14/971,355

(22) Filed: Dec. 16, 2015

(65) Prior Publication Data
US 2016/0367735 A1 Dec. 22, 2016

Related U.S. Application Data

(60) Provisional application No. 62/181,161, filed on Jun. 17, 2015.

(51) Int. Cl.
*A61B 17/20* (2006.01)
*A61M 1/00* (2006.01)
(Continued)

(52) U.S. Cl.
CPC ........... *A61M 1/0064* (2013.01); *A61F 9/007* (2013.01); *A61F 9/00745* (2013.01);
(Continued)

(58) Field of Classification Search
CPC .............. A61M 1/0058; A61M 1/0031; A61M 1/0084; A61M 2210/0612; A61M 3/0216;
(Continued)

(56) References Cited

U.S. PATENT DOCUMENTS

| 4,921,477 A | * | 5/1990 | Davis ................. A61M 1/0023 417/540 |
| 5,563,584 A | | 10/1996 | Rader et al. |

(Continued)

FOREIGN PATENT DOCUMENTS

WO 2012092018 A1 7/2012

OTHER PUBLICATIONS

International Search Report and Written Opinion for Application No. PCT/US2015/066091, dated Mar. 31, 2016, 11 pages.

*Primary Examiner* — Jason Flick
(74) *Attorney, Agent, or Firm* — Johnson & Johnson Surgical Vision, Inc.

(57) ABSTRACT

Apparatus, system and method for providing pressurized infusion of liquids and, more particularly, providing a stable and pressurized flow of fluid to the eye during surgery. Aspiration fluid may be received via an aspiration line at a first peristaltic pump, where aspiration fluid is transferred to a Venturi tank reservoir coupled to a second peristaltic pump. Fluid from a fluid source is provided via a third peristaltic pump to a pressurized infusion tank. A determination is made if the pressure in the pressurized infusion tank is at a predetermined level, where fluid may be transferred from the pressurized infusion tank to an irrigation line when pressure in the pressurized infusion tank is determined to be at the predetermined level. Alternate activation of a plurality of aspiration and irrigation lines are also provided.

21 Claims, 5 Drawing Sheets

(51) Int. Cl.
*A61F 9/007* (2006.01)
*A61M 3/02* (2006.01)
*A61M 39/22* (2006.01)

(52) U.S. Cl.
CPC ........ *A61M 1/0058* (2013.01); *A61M 1/0076* (2013.01); *A61M 3/0237* (2013.01); *A61M 39/22* (2013.01); *A61M 2205/12* (2013.01); *A61M 2205/3331* (2013.01); *A61M 2205/3341* (2013.01); *A61M 2210/0612* (2013.01)

(58) Field of Classification Search
CPC .............. A61M 1/0023; A61M 1/0064; A61M 2205/3337; A61M 2205/3344; A61M 2205/50; A61M 1/008; A61M 1/0025; A61M 2205/3331; A61M 1/0076; A61M 2205/12; A61M 2205/3341; A61M 39/22; A61M 3/0237; A61F 9/007; A61F 9/00745
USPC .................. 604/22, 65–67; 606/4, 6, 107
See application file for complete search history.

(56) References Cited

U.S. PATENT DOCUMENTS

| | | | |
|---|---|---|---|
| 5,697,898 A * | 12/1997 | Devine | A61F 9/00745 604/22 |
| 5,810,765 A * | 9/1998 | Oda | A61M 1/0058 604/22 |
| 6,511,454 B1 | 1/2003 | Nakao et al. | |
| 6,997,896 B2 * | 2/2006 | Novak | A61M 1/0058 604/67 |
| 7,018,355 B2 * | 3/2006 | Kadziauskas | A61F 9/00745 604/119 |
| 7,967,777 B2 * | 6/2011 | Edwards | A61M 1/0005 417/3 |
| 8,287,486 B2 | 10/2012 | Injev | |
| 9,445,943 B2 * | 9/2016 | Wilson | A61M 1/0064 |
| 2001/0004684 A1 * | 6/2001 | Morgan | A61M 1/0031 604/122 |
| 2002/0019601 A1 | 2/2002 | Wada | |
| 2003/0163138 A1 | 8/2003 | Nazarifar et al. | |
| 2010/0280434 A1 * | 11/2010 | Raney | A61F 9/00745 604/22 |
| 2010/0280435 A1 * | 11/2010 | Raney | A61F 9/00745 604/22 |
| 2011/0313343 A1 * | 12/2011 | Milutinovic | A61F 9/00736 604/22 |
| 2013/0131578 A1 | 5/2013 | Stalmans et al. | |
| 2013/0237900 A1 * | 9/2013 | Hauger | A61F 9/00745 604/22 |
| 2013/0245543 A1 * | 9/2013 | Gerg | A61M 1/0058 604/30 |
| 2014/0074013 A1 | 3/2014 | McCary et al. | |
| 2014/0114237 A1 | 4/2014 | Gordon | |
| 2016/0095750 A1 * | 4/2016 | Raney | A61F 9/00745 606/107 |
| 2016/0220751 A1 * | 8/2016 | Mallough | A61M 3/022 |
| 2017/0151090 A1 * | 6/2017 | Raney | A61F 9/00736 |
| 2017/0151092 A1 * | 6/2017 | Raney | A61F 9/00754 |
| 2017/0151376 A1 * | 6/2017 | Raney | A61M 1/0031 |
| 2017/0151377 A1 * | 6/2017 | Raney | A61M 1/0062 |
| 2017/0151378 A1 * | 6/2017 | Raney | A61M 1/0062 |
| 2017/0151379 A1 * | 6/2017 | Raney | A61M 1/0064 |

* cited by examiner

SYSTEM AND METHOD FOR PROVIDING PRESSURIZED INFUSION AND INCREASING OPERATING ROOM EFFICIENCY

CROSS-REFERENCE TO RELATED APPLICATIONS

This application is a non-provisional application and claims the benefit under 35 U.S.C. § 119(e) of U.S. Provisional Application Ser. No. 62/181,161, filed Jun. 17, 2015, which is incorporated herein in its entirety by reference.

BACKGROUND

Field of the Invention

The present invention relates generally to providing pressurized infusion of liquids and, more particularly, is directed to providing a stable and pressurized flow of irrigation fluid to the eye during surgery utilizing a secondary set of fluidics lines.

Description of the Background

Certain surgical procedures, such as phacoemulsification surgery, have been successfully employed in the treatment of certain ocular problems, such as cataracts. Phacoemulsification surgery utilizes a small corneal incision to insert the tip of at least one phacoemulsification handheld surgical implement, or handpiece, through the corneal incision. The handpiece includes a needle which is ultrasonically driven once placed within the incision to emulsify the eye lens, or to break the cataract into small pieces. The broken cataract pieces or emulsified eye lens may subsequently be removed using the same handpiece, or another handpiece, in a controlled manner. The surgeon may then insert a lens implant into the eye through the incision. The incision is allowed to heal, and the result for the patient is typically significantly improved eyesight.

As may be appreciated, the flow of fluid to and from a patient through a fluid infusion or extraction system, and thus the control of fluids and fluid pressure through the phacoemulsification handpiece, is critical to the procedure performed. Different medically recognized techniques have been utilized to control the fluid flow during the lens removal portion of the surgery. Among these, one popular technique is a simultaneous combination of phacoemulsification, irrigation and aspiration using a single handpiece. This method includes making the incision, inserting the handheld surgical implement to emulsify the cataract or eye lens, and, simultaneously with this emulsification, having the handpiece provide a fluid for irrigation of the emulsified lens and a vacuum for aspiration of the emulsified lens and inserted fluids.

Currently available phacoemulsification systems, such as those mentioned above, typically include a variable speed peristaltic pump and/or vacuum pump, a vacuum sensor, an adjustable source of ultrasonic power, and a programmable microprocessor with operator-selected presets for controlling aspiration rate, vacuum and ultrasonic power levels. The phacoemulsification handpiece is interconnected with a control console by an electric cable for powering and controlling a piezoelectric transducer that drives the action of the handpiece. Tubing provides irrigation fluid to the eye through the handpiece and enables withdrawal of aspiration fluid from an eye through the handpiece.

Generally, irrigation and aspiration are employed by the surgeon using the device to remove unwanted tissue and maintain pressure within the eye. Moreover, the use of, and particularly the pressurization of, the irrigation fluid is critical and may, for example, prevent the collapse of the eye during the removal of the emulsified lens. Irrigation fluid pressure is also used to protect the eye from the heat generated by the ultrasonic cutting needle and may suspend fragments created during the surgery in fluid for more easy removal through aspiration.

Irrigation fluid pressure has been conventionally handled in two ways. The first method to increase irrigation fluid pressure has relied upon the height of the fluid source. Conventional IV poles may be adjusted in height to create the desired pressure head using gravity-feed principles. The second method includes the use of an infusion pump either directly pumping the fluid typically in the form of a peristaltic pump used in-line with an irrigation delivery line or by pressurizing the fluid container thus increasing higher atmosphere above the fluid resulting in higher infusion pressure and flow to the surgical site.

Furthermore, alone or in conjunction with the methods discussed above, the fluid pressure within the fluid source may be adjusted by compression which may be internal and/or external to the fluid source. For example, an IV bag may be physically compressed by at least two opposed plates which may exert a force on the bag sufficient to provide for a fluid pressure above a simple gravity feed. The compression of the fluid may be dynamic to allow for a consistent and/or specific pressure as the volume of fluid decreases in the IV bag. Pressure may also be provided internal to the fluid source by the introduction of a higher pressure, such as using an inert gas, for example.

Although each of the foregoing methods produces pressurized irrigation fluid at the surgical site, each suffers from difficulties in maintaining a constant pressure. For example, infusion pumps must be deployed with a dynamic pressure-sensing control loop to prevent over or under pressurizing the anterior chamber, and may further require venting to control unwanted pressures. Solving these issues may require the use of a special drip spike, a mechanical pressurization compartment, or an over-bag, to control atmospheric pressure. Such solutions add costs and complications to the surgical set-up and to the maintenance of the surgical equipment.

Further, it is typical that the smaller the incision made during surgery, the greater the pressure needed to properly irrigate the surgical site, and gravity-feed systems may not produce the desired amount of pressure due at least to limitations on the height which may be achieved by physically raising the source of irrigation liquid. Typically, the irrigation source is affixed to a movable IV pole which is raised to increase the pressure head. Of course, limitations as to the maximum height of the IV pole and/or the height of overhead objects, such as lights or a ceiling, for example, may limit the amount of achievable height.

Moreover, in the aforementioned configurations combining phacoemulsification, irrigation and aspiration, the handpiece may be configured to provide a fluid for irrigation of an emulsified lens and a vacuum for aspiration of the emulsified lens and inserted fluids. In such configurations fluidics lines are typically switched from phacoemulsification to irrigation and aspiration. While the configuration provides advantages for the surgical procedure, the switching of fluidics lines unnecessarily slows down the procedure and creates the potential for fluid to drain accidentally. Furthermore, the switching of lines has the tendency to introduce fluctuations of intra-ocular pressure.

Thus, there is a need for a system and method that provides improved pressurized delivery of irrigation fluid to a surgical site.

SUMMARY OF THE INVENTION

The present disclosure is directed to a system and a method of providing pressurized fluid to the eye. The system and method may include at least one constant pressure source and at least one height adjustable irrigation fluid source to provide a stable pressurized fluid flow.

In one embodiment, a secondary set of fluidics lines are provided to allow phacoemulsification, irrigation and aspiration handpieces to be primed and ready for surgery simultaneously. A tertiary peristaltic pump and an additional fluid reservoir may be provided to pressurize a balanced salt solution (BSS) bag. The system software, tangibly embodied in hardware, would allow a surgeon to select a desired inter-ocular pressure and would then control the pumps and valves to achieve and maintain the selected pressure.

Accordingly, the disclosure provides a system and method that provides improved pressurized delivery of irrigation fluid to a surgical site.

DESCRIPTION OF THE DRAWINGS

The accompanying drawings are included to provide a further understanding of the invention, and are incorporated in and constitute a part of this specification. The drawings illustrate disclosed embodiments and/or aspects and, together with the description, serve to explain the principles of the invention, the scope of which is determined by the claims.

In the drawings.

DETAILED DESCRIPTION OF THE INVENTION

It is to be understood that the FIG.s and descriptions of the present invention have been simplified to illustrate elements that are relevant for a clear understanding of the present invention, while eliminating, for the purpose of clarity, many other elements found in typical surgical, and particularly optical surgical, apparatuses, systems, and methods. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to the disclosed elements and methods known to those skilled in the art.

Figure 1:
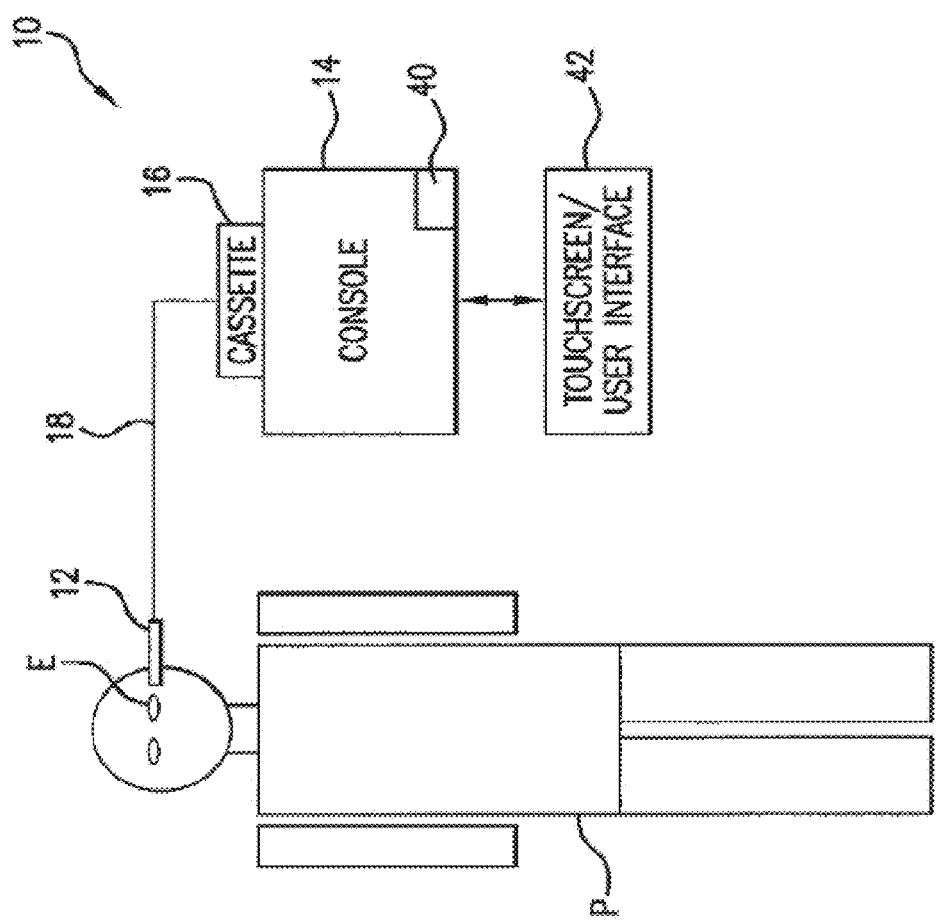
FIG. 1 schematically illustrates an eye treatment system in which a cassette couples an eye treatment probe with an eye treatment console, along with a method for use of the system for treating the eye of a patient.

Referring to FIG. 1, a system 10 for treating an eye E of a patient P generally includes an eye treatment probe handpiece 12 coupled to a console 14 by a cassette 16 mounted on the console. Handpiece 12 generally includes a handle for manually manipulating and supporting an insertable probe tip. The probe tip has a distal end which is insertable into the eye, with one or more lumens in the probe tip allowing irrigation fluid to flow from the console 14 and/or cassette 16 into the eye. Aspiration fluid may also be withdrawn through a lumen of the probe tip, with the console 14 and cassette 16 generally including a vacuum aspiration source, a positive displacement aspiration pump, or both to help withdraw and control a flow of surgical fluids into and out of eye E. As the surgical fluids may include biological materials that should not be transferred between patients, cassette 16 will often comprise a disposable (or alternatively, sterilizable) structure, with the surgical fluids being fed through flexible conduits 18 of the cassette that avoid direct contact in between those fluids and the components of console 14.

When a distal end of the probe tip of handpiece 12 is inserted into an eye E (for example) for removal of a lens of a patient with cataracts, an electrical conductor (not shown) may supply energy from console 14 to an ultrasound transmitter of the handpiece. Alternatively, the handpiece 12 may be configured as an I/A or vitrectomy handpiece. Also, the ultrasonic transmitter may be replaced by other means for emulsifying a lens, such as a high energy laser beam. The ultrasound energy from handpiece 12 helps to fragment the tissue of the lens, which can then be drawn into a port of the tip by aspiration flow. So as to balance the volume of material removed by the aspiration flow, an irrigation flow through handpiece 12 (or a separate probe structure) may also be provided, with both the aspiration and irrigations flows being controlled by console 14.

So as to avoid cross-contamination between patients without incurring excessive expenditures for each procedure, cassette 16 and its flexible conduit 18 may be disposable. Alternatively, the flexible conduit or tubing may be disposable, with the cassette body and/or other structures of the cassette being sterilizable. Regardless, the disposable components of the cassette are typically configured for use with a single patient, and may not be suitable for sterilization. The cassette will interface with reusable (and often quite expensive) components of console 14, including peristaltic pump rollers, a Venturi or other vacuum source, a controller 40, and the like.

Controller 40 may include an embedded microcontroller and/or many of the components of a personal computer, such as a processor, a data bus, a memory, input and/or output devices (including a touch screen user interface 42), and the like. Controller 40 will often include both hardware and software, with the software typically comprising machine readable code or programming instructions for implementing one, some, or all of the methods described herein. The code may be embodied by a tangible media such as a memory, a magnetic recording media, an optical recording media, or the like. Controller 40 may have (or be coupled to) a recording media reader, or the code may be transmitted to controller 40 by a network connection such as an internet, an intranet, an Ethernet™, a wireless network, or the like. Along with programming code, controller 40 may include stored data for implementing the methods described herein, and may generate and/or store data that records parameters corresponding to the treatment of one or more patients. Many components of console 14 may be found in or modified from known commercial phacoemulsification systems from Abbott Medical Optics Inc. of Santa Ana, Calif.;

Alcon Manufacturing, Ltd. of Ft. Worth, Tex., Bausch and Lomb of Rochester, N.Y., and other suppliers.

Figure 2:
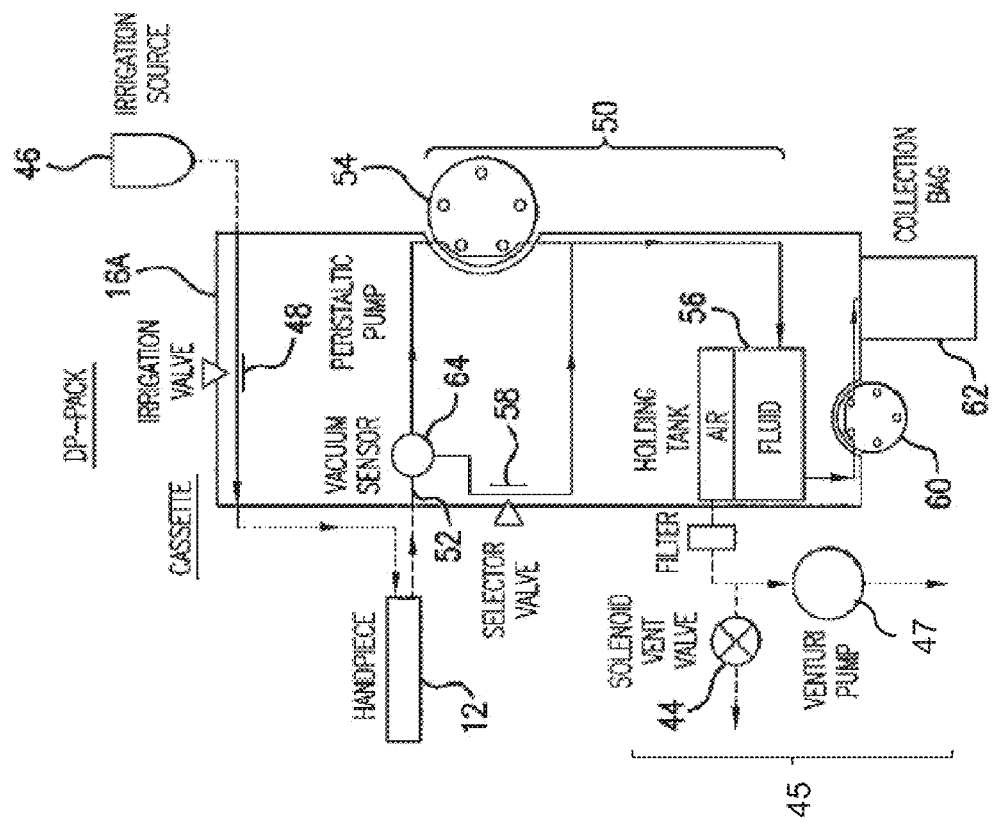
FIG. 2 schematically illustrates a dual mode cassette having a surgical fluid pathway network for use in the system of FIG. 1.

Referring now to FIGS. 1 and 2, components of the aspiration and irrigation fluid flow networks of system 10 are described in more detail with respect to a dual mode or dual pump cassette 16A that enables both displacement-based and vacuum-based aspiration modes. FIG. 2 generally highlights the surgical aspiration and irrigation fluid control elements included within the cassette 16A, with the irrigation components often being relatively straightforward. An irrigation source 46 of the console optionally provides irrigation fluid pressure control by relying at least in part on a gravity pressure head that varies with a height of an irrigation fluid bag or the like. An irrigation on/off pinch valve 48 may generally include a short segment of a flexible conduit of cassette 16A, which can be engaged and actuated by an actuator of the console 14, e.g. with a surface of the cassette body often being disposed opposite the actuator to facilitate closure of the conduit lumen. Alternative irrigation flow systems may include positive displacement pumps, alternative fluid pressurization drive systems, fluid pressure or flow modulating valves, and/or the like. In certain embodiments, irrigation fluid is alternatively or additionally provided to a separate handpiece (not shown).

The aspiration flow network 50 generally provides an aspiration flow path 52 that can couple an aspiration port in the tip of handpiece 12 to either a peristaltic pump 54 and/or to a fluid container or holding tank 56. Fluid aspirated through the handpiece 12 may be contained in the holding tank 56 regardless of whether the aspiration flow is induced by peristaltic pump 54 or the vacuum applied to the holding tank 56. When valve 58 is closed and peristaltic pump 54 is in operation, pumping of the aspiration flow may generally be directed by the peristaltic pump 54, independent of the pressure in the holding tank 56. Conversely, when peristaltic pump 54 is off, flow through the peristaltic pump may be halted by pinching of the elastomeric tubing arc of the peristaltic pump by one or more of the individual rollers of the peristaltic pump rotor. Hence, any aspiration fluid drawn into the aspiration network when peristaltic pump 54 is off will typically be affected by opening of a valve 58, which may be a selector control valve so that the aspiration port of the probe is in fluid communication with the holding tank. Regardless, the pressure within tank 56 may be maintained at a controlled vacuum level, often at a fixed vacuum level, by a vacuum system 45 of the console. The vacuum system 45 may comprise a Venturi pump 47, a rotary vane pump, a vacuum source, or the like, and a vent valve 44. Aspiration flow fluid held into holding tank 56 may be removed by a peristaltic drain pump 60 and directed to a disposal fluid collection bag 62. Vacuum pressure at the surgical handpiece may be maintained within a desired range through control of the fluid level in the holding tank.

In more detail, the operation of aspiration flow network 50 can be understood by first considering the flow when valve 58 is closed. In this mode, peristaltic pump 54 draws fluid directly from handpiece 12, with a positive displacement peristaltic pump flow rate being controlled by the system controller 40 (see FIG. 1). To determine the appropriate flow rate, the level of vacuum within the aspiration flow network may be identified in part with reference to a vacuum sensor 64 disposed along the aspiration flow network 50 between peristaltic pump 54 and handpiece 12. This allows the system to detect and adjust for temporary occlusions of the handpiece and the like. While the aspiration material flows through holding tank 56 and eventually into collection bag 62, the holding tank pressure may have little or no effect on the flow rate in this mode.

When peristaltic pump 54 is not in operation, rotation of the peristaltic pump is inhibited and the rotors of the peristaltic pump pinch the arcuate resilient tubing of the probe so as to block aspiration flow. Material may then be drawn into the aspiration port of handpiece 12 by opening selector valve 58 and engagement or operation of the vacuum system 45. When valve 58 is open, the aspiration port draws fluid therein based on the vacuum in the holding tank 56 Aspiration network 50 of the dual mode cassette 16A allows system 10 to operate in either peristaltic or vacuum-based pumping modes.

Figure 3:
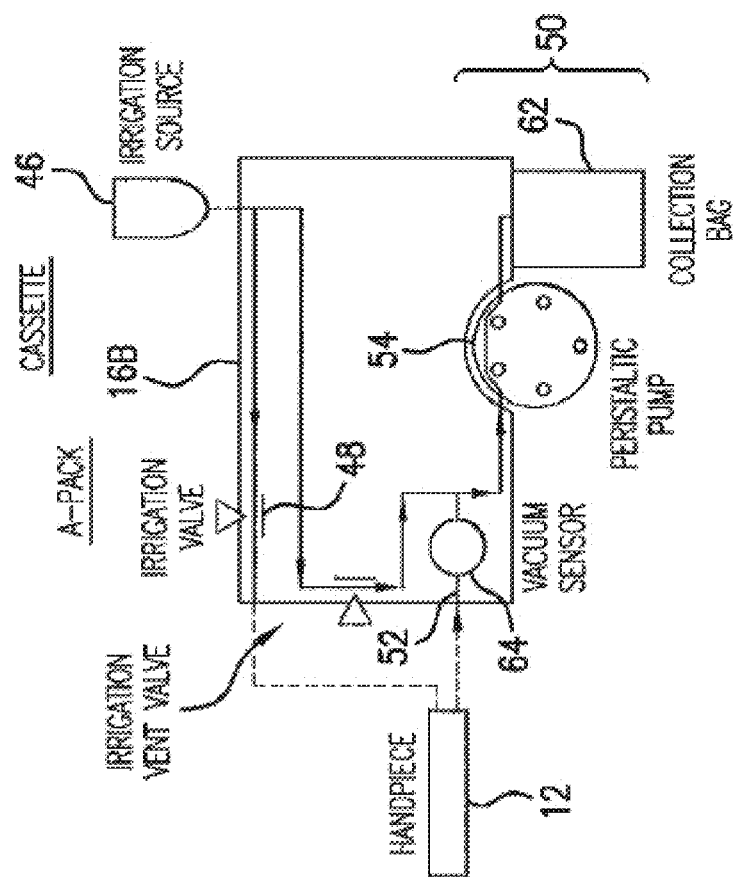
FIG. 3 schematically illustrates a single mode displacement-based aspiration cassette having a surgical fluid pathway network for use in the system of FIG. 1.

When only displacement-based pumping will be used for a particular procedure, an alternative cassette may be employed in the console 14, with the alternative cassette lacking a holding tank 56, selector valve 58, and the like. Referring now to FIGS. 1 and 3, components of a single mode cassette 16B are described, the single mode cassette enabling only the displacement-based aspiration mode. Within the single mode cassette, peristaltic pump 54 draws fluid directly from handpiece 12, with a positive displacement peristaltic pump flow rate being controlled by the system controller 40 (see FIG. 1). To determine the appropriate flow rate, the level of vacuum within the aspiration flow network may be identified in part with reference to a vacuum sensor 64 disposed along the aspiration flow network 50 between peristaltic pump 54 and handpiece 12. The aspiration material flows directly into collection bag 62. Alternatively, a single mode cassette may also be provided that only enables vacuum-based aspiration.

As a dual mode cassette may be somewhat more complex, a single mode cassette may be both simpler and less expensive. Therefore, the present invention may avoid complexity and provide cost savings by enabling the use of a less expensive single mode cassette when only a single aspiration mode is needed during a procedure on a particular patient.

Figure 4:
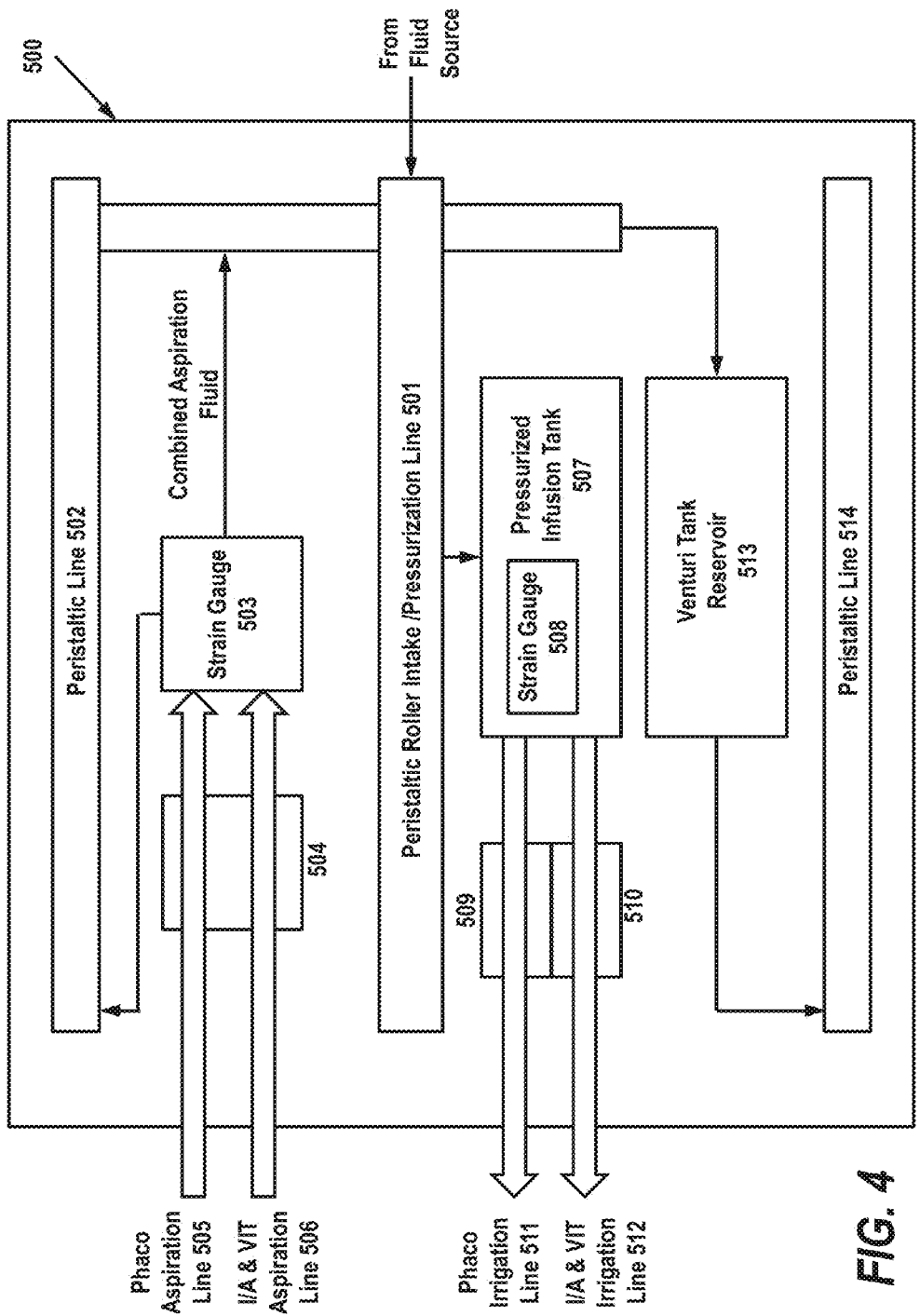
FIG. 4 illustrates a block diagram of a pressurized infusion pack under one exemplary embodiment.
Figure 5:
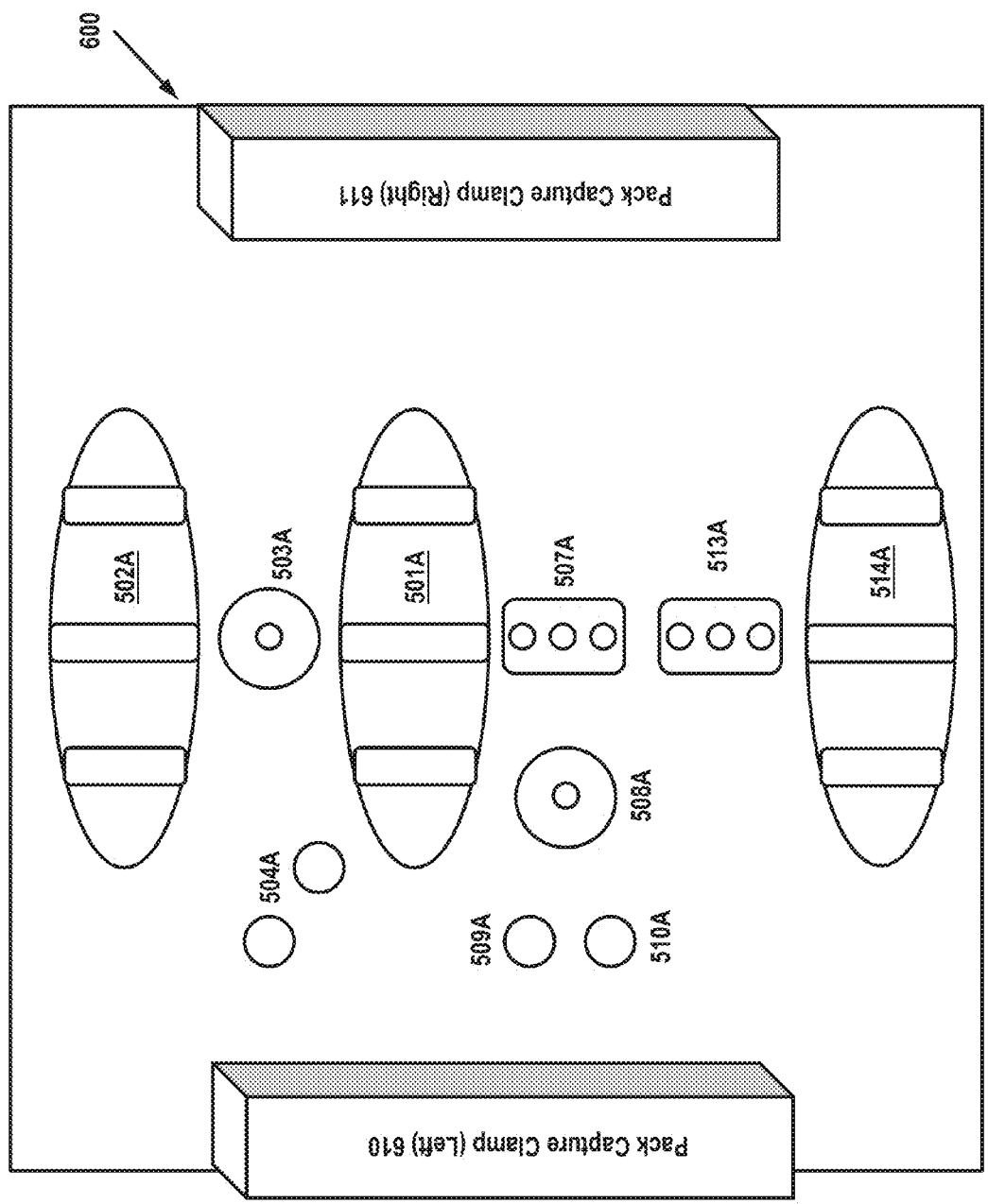
FIG. 5 illustrates an exemplary interface for the pressurized infusion pack of FIG. 4 under one embodiment.

Turning now to FIGS. 4 and 5, an exemplary pressurized infusion pack 500 and console interface 600 with left/right pack capture clamps 610-611, is illustrated, comprising a first peristaltic line 502, a second peristaltic line 514 and a tertiary peristaltic line 501, wherein each may interface with pumps 502A, 514A and 501A respectively located on console interface 600 as shown in FIG. 5. Pump 502A may comprise a peristaltic pump that mates with peristaltic line 502, and may serve as a primary means of moving fluid through the system and a prospective patient's eye in the event that the system is being used in peristaltic mode or Venturi mode.

An initial fluid intake line (from a balanced salt solution (BSS) source) may be provided to line 501, which would contact a roller head 501A as shown in FIG. 5. The line and the roller head may be configured to be the driving force for creating fluid pressure. Line 514 may be configured as the last section of an aspiration line, which would mate with peristaltic pump 514A, which may act as a drain pump to remove fluid from Venturi reservoir 513 when fluid level within the tank is too high.

Phacoemulsification aspiration line 505, and irrigation and aspiration (I/A) and vitrectomy line 506 are configured to enter strain gauge 503 via pinch valve receptor 504, where the aspiration lines may comprise used BSS fluid. In an embodiment, pinch valves 504A and 504B, located on console interface 600 as shown in FIG. 6, may be received on either side of strain gauge 503. Depending on the surgical mode being utilized, one of the two pinch valves, for example 504A, may be energized to prevent fluid flow from an inactive line. Strain gauge 503 may be coupled to mating surface 503A of FIG. 5 in order to measure a vacuum present in the aspiration lines. Combined aspiration fluid may be transferred as shown in FIG. 4 to Venturi tank reservoir 513. Fluid level in Venturi tank 513 may be monitored via LEDs 513A or other suitable visual indicia.

Pressurized infusion tank 507 may be configured to store pressurized fluid, where strain gauge 508 and mating surface 508A may allow strain gauge 508 to measure pressure inside the pressurized infusion tank 507. Fluid level in pressurized infusion tank 507 may be monitored via LEDs 507A or other suitable visible indicia. Irrigation from pressure infusion tank 507 is provided via phacoemulsification irrigation line 511, and I/A and vitrectomy irrigation line 512 as shown in FIG. 4. Pinch valve receptors 509-510, for receiving pinch valves 509A and 510A, located on console interface 600 as shown in FIG. 6, may be energized to cut off fluid supply from inactive lines.

Accordingly, pressurized infusion pack 500 may be configured to provide three methods of introducing fluid to the surgical area: peristaltic, Venturi and pressurized infusion. In the cases of Venturi and peristaltic, the pack may operate in a manner similar to that described above, except that pressurized infusion pack 500 may utilize peristaltic pump 501, which may be configured in the center of the fluidics panel. In one embodiment, at least one roller head associated with peristaltic pump 501 may be temporarily disengaged from the fluid line to provide more control over the pressure within the line.

For pressurized infusion, infusion tank 507, arranged above Venturi tank reservoir 513, is configured to build pressure, where the system would make use of tertiary peristaltic roller from 501 to push fluid from the fluid source into tank 507. The fluid may be held inside tank 507 utilizing pinch valves 509A, 510A on the outgoing irrigation lines 511, 512. When sufficient pressure and fluid volume is present, at least one of pinch valves 509, 510 may be released to allow fluid to move through the lines at a user's desired pressure.

As mentioned above, pressure may be measured (+mmHg) utilizing strain gauge 508 which may be configured to be inside tank 507. The system may additionally utilize measurements from strain gauge 503 (−mmHg) to ensure that pressure within an eye has not become too high or too low.

One of the advantages of the disclosed configuration is that having two sets of fluidics tubing may allow end users to simultaneously prime a phacoemulsification handpiece and an I/A handpiece, such that they may be prepared for use in surgery simultaneously. One skilled in the art would recognize that this advantageously saves users time and potential frustration from changing lure fittings at least once during a procedure.

In one embodiment, lures and tubing of one fluidics tubing set may be configured for the phacoemulsification handpiece, while the other set would be configured for the irrigation and aspiration handpiece. The tubing may advantageously be color coded for ease of use. During surgery, only one set of lines would be active at one time under one embodiment. When a user selects phacoemulsification, the pinch valves would operate as normal for the phacoemulsification fluidics lines, while the pinch valves for the I/A fluidics lines would energize and prevent any flow from those lines. Similarly, when a user selects the I/A handpiece (or vitrectomy), the pinch valves for those modes would act as normal while pinch valves for the phacoemulsification fluidics energize to prevent further flow.

Those of ordinary skill in the art may recognize that many modifications and variations of the herein disclosed systems and methods may be implemented without departing from the spirit or scope of the invention. Thus, it is intended that the present invention covers such modifications and variations provided they come within the scope the appended claims and their equivalents.

What is claimed is:

1. A method for providing pressurized fluid to an eye, comprising:
   receiving aspiration fluid via an aspiration line at a first pump configured to receive aspiration fluid via an aspiration line arrangement to a reservoir;
   providing a second pump configured to transmit fluid from a fluid source to a pressurized infusion tank;
   automatically determining if pressure in the pressurized infusion tank is at a predetermined level; and
   transferring fluid from the pressurized infusion tank to an irrigation line when pressure in the pressurized infusion tank is automatically determined to be at the predetermined level.

2. The method of claim 1, wherein the first pump is either a peristaltic pump or a Venturi pump.

3. The method of claim 1, wherein the second pump is either a peristaltic pump or a Venturi pump.

4. The method of claim 1, wherein automatically determining if the pressure in the pressurized infusion tank is at the predetermined level comprises automatically measuring the pressure via a gauge coupled with the pressurized infusion tank.

5. The method of claim 1, wherein the aspiration line comprises at least one of a phacoemulsification aspiration line, an irrigation and aspiration line, and a vitrectomy aspiration line.

6. The method of claim 1, wherein the irrigation line comprises at least one of a phacoemulsification irrigation line, an irrigation and aspiration line, and a vitrectomy irrigation line.

7. The method of claim 1, wherein transferring fluid from the pressurized infusion tank to the irrigation line comprises opening a pinch valve coupled to the irrigation line when pressure in the pressurized infusion tank is determined to be at the predetermined level.

8. The method of claim 1, further comprising measuring the pressure at the aspiration line to determine if the aspiration pressure is at a predetermined level.

9. The method of claim 7, further comprising transferring fluid from the pressurized infusion tank to the irrigation line when the aspiration pressure and the pressure in the pressurized infusion tank are automatically determined to be at the respective predetermined levels.

10. A system for providing pressurized fluid to an eye, comprising:
    a first peristaltic pump configured to receive aspiration fluid via an aspiration line arrangement to a reservoir;
    a second peristaltic pump configured to provide fluid from a fluid source to a pressurized infusion tank;
    a pressure measurement apparatus configured to automatically determine if pressure in the pressurized infusion tank is at a predetermined level; and
    a valve apparatus configured to transfer fluid from the pressurized infusion tank to an irrigation line arrangement when pressure in the pressurized infusion tank is automatically determined to be at the predetermined level.

11. The system of claim 10, wherein the pressure measurement apparatus comprises a gauge operatively coupled with the pressurized infusion tank and configured to automatically determine if pressure in the pressurized infusion tank is a predetermined level.

12. The system of claim 10, wherein the aspiration line arrangement comprises at least one of a phacoemulsification aspiration line, an irrigation and aspiration line, and a vitrectomy aspiration line.

13. The system of claim 10, wherein the irrigation line arrangement comprises at least one of a phacoemulsification irrigation line, an irrigation and aspiration line, and a vitrectomy irrigation line.

14. The system of claim 10, wherein the valve apparatus comprises a pinch valve coupled to the irrigation line, the pinch valve being configured to open to allow flow when pressure in the pressurized infusion tank is automatically determined to be at the predetermined level.

15. The system of claim 10, further comprising a second pressure measurement apparatus configured to measure the pressure at the aspiration line arrangement to automatically determine if the aspiration pressure is at a predetermined level.

16. The system of claim 15, wherein the valve apparatus is configured to transfer fluid from the pressurized infusion tank to the irrigation line when the aspiration pressure and the pressure in the pressurized infusion tank are automatically determined to be at the respective predetermined levels.

17. A system for providing pressurized fluid to an eye, comprising:
a first peristaltic pump, operatively coupled to a phacoemulsification aspiration line and a non- phacoemulsification aspiration line via a first pinch valve apparatus,
wherein the phacoemulsification aspiration line and non-phacoemulsification aspiration line are coupled with a reservoir;
a second peristaltic pump operatively coupled to a fluid source and configured to provide fluid from the fluid source to a pressurized infusion tank, the pressurized infusion tank being operatively coupled to a phacoemulsification irrigation line and a non- phacoemulsification irrigation line via a second pinch valve apparatus,
wherein the system is configured to energize at least a portion of the first and second pinch valve apparatus to at least one of:
activate the phacoemulsification aspiration line and phacoemulsification irrigation line, while preventing flow from the non-phacoemulsification aspiration line and non-phacoemulsification irrigation line, and
activate the non-phacoemulsification aspiration line and non-phacoemulsification irrigation line, while preventing flow from the phacoemulsification aspiration line and phacoemulsification irrigation line.

18. The system of claim 17, wherein the non-phacoemulsification aspiration line comprises one of (i) an irrigation and aspiration line, and (ii) a vitrectomy irrigation line.

19. The system of claim 17, wherein the non-phacoemulsification irrigation line comprises one of (i) an irrigation and aspiration line, and (ii) a vitrectomy irrigation line.

20. The system of claim 17, further comprising a phacoemulsification handpiece operatively coupled to the phacoemulsification aspiration line and phacoemulsification irrigation line.

21. The system of claim 17, further comprising an irrigation and aspiration handpiece operatively coupled to the non-phacoemulsification aspiration line and non-phacoemulsification irrigation line.

* * * * *